United States Patent
Trapp et al.

(10) Patent No.: US 11,389,908 B2
(45) Date of Patent: Jul. 19, 2022

(54) SYSTEMS AND METHODS FOR DETECTING WELD BEAD CONFORMITY

(71) Applicant: Dexter Stamping Company, LLC, Jackson, MI (US)

(72) Inventors: Christopher Lyman Trapp, Jackson, MI (US); Dexter Alexander Smith, Jackson, MI (US)

(73) Assignee: Dexter Stamping Company, LLC, Jackson, MI (US)

(*) Notice: Subject to any disclaimer, the term of this patent is extended or adjusted under 35 U.S.C. 154(b) by 0 days.

(21) Appl. No.: 17/265,299

(22) PCT Filed: Aug. 2, 2019

(86) PCT No.: PCT/US2019/044904
§ 371 (c)(1),
(2) Date: Feb. 2, 2021

(87) PCT Pub. No.: WO2020/028802
PCT Pub. Date: Feb. 6, 2020

(65) Prior Publication Data
US 2021/0316404 A1    Oct. 14, 2021

Related U.S. Application Data

(60) Provisional application No. 62/713,843, filed on Aug. 2, 2018.

(51) Int. Cl.
*B23K 31/12* (2006.01)
*H04N 5/232* (2006.01)
(Continued)

(52) U.S. Cl.
CPC ......... *B23K 31/125* (2013.01); *G01N 33/207* (2019.01); *G06T 7/001* (2013.01); *H04N 5/23299* (2018.08); *G06T 2207/30136* (2013.01)

(58) Field of Classification Search
CPC .... B23K 31/125; B23K 9/0956; B23K 9/167; B23K 9/173; G01N 33/207; H04N 5/23299
See application file for complete search history.

(56) References Cited

U.S. PATENT DOCUMENTS

| 5,533,146 A | * | 7/1996 | Iwai | ..................... B23K 9/0956 |
| | | | | 348/90 |
| 2018/0065204 A1 | * | 3/2018 | Burrows | ................ B25J 11/007 |

FOREIGN PATENT DOCUMENTS

JP    2013068580 A  *  4/2013  ............. G01B 11/24

OTHER PUBLICATIONS

International Search Report dated Nov. 13, 2019 pertaining to PCT Application No. PCT/US2019/044904, 3 pages.
(Continued)

*Primary Examiner* — Dakshesh D Parikh
(74) *Attorney, Agent, or Firm* — Dinsmore & Shohl LLP

(57) ABSTRACT

Embodiments described herein are for determining a weld quality by an imaging device configured to generate one or more signals indicative of a weld bead positioned on at least one part. Machine-readable instruction set causes a computing device to perform at least the following when executed by the processor: capture an initial scan to determine a plurality of offset information based on predetermined part features, activate the imaging device to capture a scan of the weld bead, establish a line scan profile of the weld bead, determine that the scan of the weld bead matches a predetermined weld model, and analyze the weld bead profile to determine a volume of the weld bead, a rising edge of the weld bead, and a falling edge of the weld bead and comparing the weld bead profile to a plurality of predetermined parameters for the weld bead to determine a satisfactory weld quality.

20 Claims, 14 Drawing Sheets
(9 of 14 Drawing Sheet(s) Filed in Color)

(51) Int. Cl.
*G01N 33/207* (2019.01)
*G06T 7/00* (2017.01)

(56) References Cited

OTHER PUBLICATIONS

Written Opinion dated Nov. 13, 2019 pertaining to PCT Application No. PCT/US2019/044904, 6 pages.

\* cited by examiner

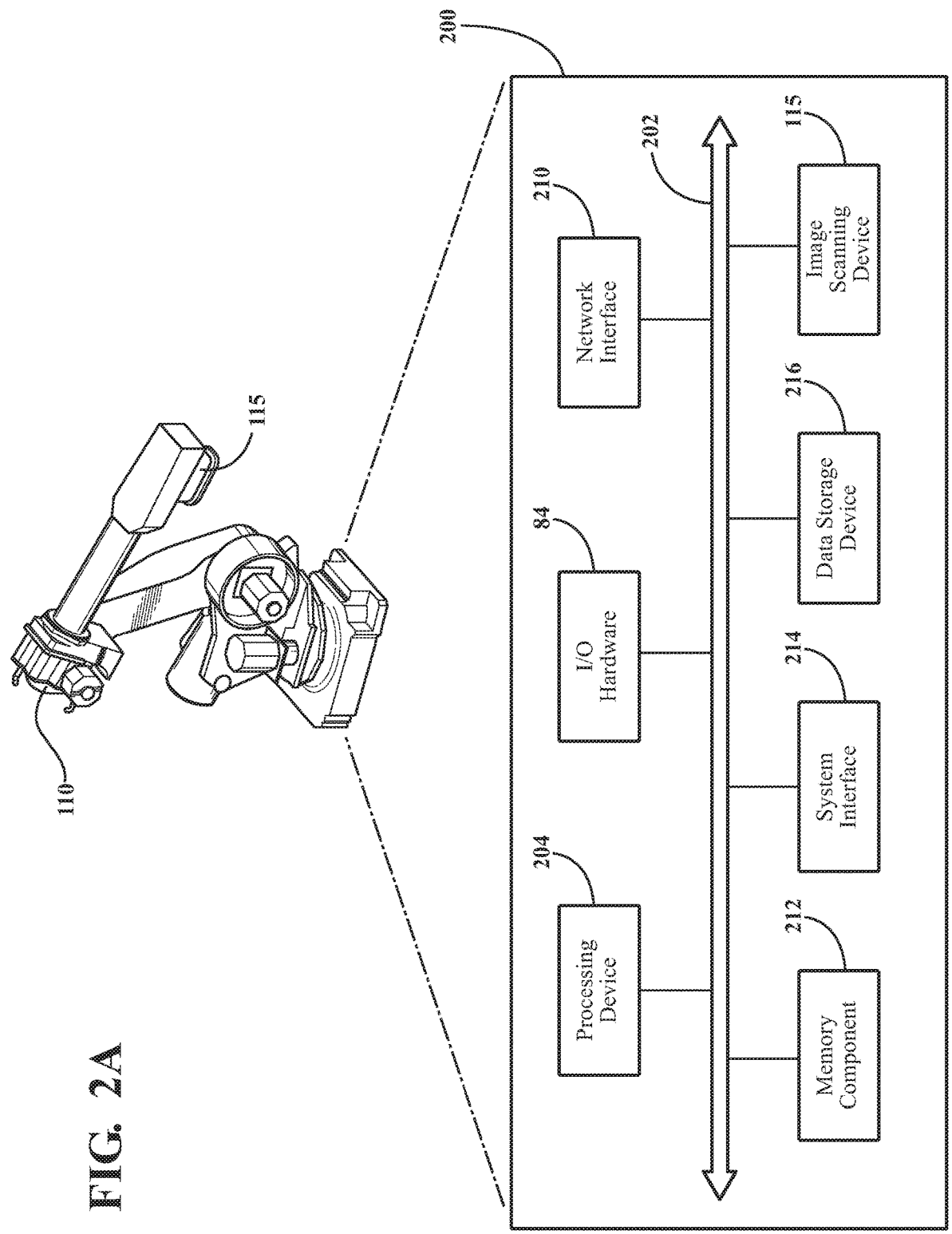

SYSTEMS AND METHODS FOR DETECTING WELD BEAD CONFORMITY

CROSS REFERENCE TO RELATED APPLICATIONS

This utility patent application claims priority from U.S. Provisional Patent Application Ser. No. 62/713,843, filed on Aug. 2, 2018, the entire contents of which is incorporated herein in its entirety.

TECHNICAL FIELD

The present disclosure generally relates to quality of weld beads and, more particularly, to systems and methods for detecting weld bead conformity by analyzing a line scan of the weld bead to determine rising and falling edges height and a volume of the weld bead.

BACKGROUND

As background, a welding process is used to join a first component, typically made of metal material, to a second part component, typically made of a metal material. The abutting surfaces of the two components are typically brought to a molten state such that a weld bead is formed at the abutting surfaces. The weld bead may be performed by several different techniques such as mig welders, tig welders, and/or the like such that the weld bead may be created by a gas flame, an electric arc, a chemical reaction, electrical resistance, and/or the like.

A weld bead generally has a filler that is posited in the molten area of the abutting surfaces and has a weld toe zone or region formed on each side of the filler. The upper most surface of the weld bead, the portion generally exposed, is a face portion. The characteristics of the weld bead are important to monitor to know that the weld bead meets certain quality standards based on predetermined parameters. One such characteristic of the weld bead is the height that the face of the weld bead is raised from the abutting surfaces of the part components. Another characteristic of the weld bead is the length that the face of weld bead is raised from the abutting surfaces of the part components. With these characteristics known, a volume of the weld bead may be determined. If the weld bead face does not extend vertically enough or does not travel enough of the length of the abutting surfaces, the weld bead may be fragile because there is not enough volume of filler material or reinforcement in the weld bead.

Accordingly, it would be desirable to have an automated process that monitors the weld bead quality by focusing on the face height and the face length of the weld bead.

SUMMARY

In one embodiment, a system for determining a weld quality is provided. The system includes a robot having an imaging device configured to generate one or more signals indicative of a weld bead positioned on at least one part, a computing device communicatively coupled to the imaging device, and a machine-readable instruction set stored in the non-transitory computer-readable memory. The computing device includes a processor and a non-transitory computer readable memory. The machine-readable instruction set stored in the non-transitory computer-readable memory that causes the computing device to perform at least the following when executed by the processor: capture an initial scan to determine a plurality of offset information based on predetermined part features, activate the imaging device to capture a scan of the weld bead, establish a line scan profile of the weld bead, determine that the scan of the weld bead matches a predetermined weld model, and analyze the weld bead profile to determine a volume of the weld bead, a rising edge of the weld bead, and a falling edge of the weld bead. The volume, the rising edge and the falling edge of the weld bead are used to determine that the weld bead has a satisfactory weld quality by comparing the volume, the rising edge and the falling edge of the weld bead to a plurality of predetermined parameters for the weld bead. When the comparison of the weld bead to the plurality of predetermined parameters is indicative of the satisfactory weld quality, the at least one part is permitted to be advanced by the robot.

In another embodiment, a method of determining a weld quality between at least two parts sharing a weld bead is provided. The method includes capturing an initial scan of the at least two parts to determine a plurality of offset information based on predetermined part features, positioning a robot having an imaging device to scan the weld bead based on the plurality of offset information, activating the imaging device to capture a scan of the weld bead, establishing a line scan profile of the weld bead, determining that the scan of the weld bead matches a predetermined weld model, and analyzing the weld bead profile to determine a volume of the weld bead, a rising edge of the weld bead, and a falling edge of the weld bead.

In yet another embodiment, a system for determining a weld quality is provided. The system includes a robot having an imaging device configured to generate one or more signals indicative of a quality of a weld bead joining at least two parts into a combined part, a computing device communicatively coupled to the imaging device, and a machine-readable instruction set stored in the non-transitory computer-readable memory. The computing device includes a processor and a non-transitory computer readable memory. The machine-readable instruction set stored in the non-transitory computer-readable memory that causes the computing device to perform at least the following when executed by the processor: capture an initial scan of the at least two parts to determine a plurality of offset information based on predetermined part features, position a robot having an imaging device to scan the weld bead based on the plurality of offset information, activate the imaging device to capture a scan of the weld bead, establish a line scan profile of the weld bead, determine that the scan of the weld bead matches a predetermined weld model, analyze the weld bead profile to determine a volume of the weld bead, a rising edge of the weld bead, and a falling edge of the weld bead, and compare the volume of the weld bead, the rising edge of the weld bead, and the falling edge of the weld bead to predetermined parameters such that a positive comparison of the weld bead to the plurality of predetermined parameters is indicative of the satisfactory weld quality. In response, the combined part is permitted to be advanced by the robot.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The embodiments set forth in the drawings are illustrative and example in nature and not intended to limit the subject matter defined by the claims. The following detailed description of the illustrative embodiments can be understood when read in conjunction with the following drawings, wherein like structure is indicated with like reference numerals and in which:

FIG. 2A schematically depicts illustrative hardware components of a computing device that may be used in scanning and measuring the weld bead according to one or more embodiments shown and described herein;

DETAILED DESCRIPTION

Embodiments of the present disclosure are directed to systems and methods for scanning and measuring a height of a face of a weld bead, which is raised from an abutting surface of two components, and a length that the face of the weld bead is raised from the abutting surfaces of the components. The disclosed system determines the position of the weld bead by scanning a predetermined feature of at least one component so to calibrate, or position a line scanning device with an offset in reference to the known feature. Once aligned, the line scanning device scans any weld bead in a predetermined routine.

Once the scan of the weld bead is complete, the system creates a line scan profile of the weld bead so to determine whether the weld bead meets predetermined quality parameters. As such, the system uses the line scan profile to analyze the line scan of the weld bead. For instance, the system may determine the length that the face of the weld bead travels along the abutted surfaces, determine the height of the face of the weld bead, determine the height and/or slope that the face is raised from the abutting surfaces at a rising edge and a falling edge, determine a volume of the weld bead, and/or the like. The system may reject the weld bead, and ultimately the part components, based on whether any of these determinations are found to have deficiencies when compared to predefined parameters.

Various systems and methods for detecting a weld quality and either physically rejecting the parts and/or allowing the parts to continue in the assembly process are described in detail herein.

Figure 3:
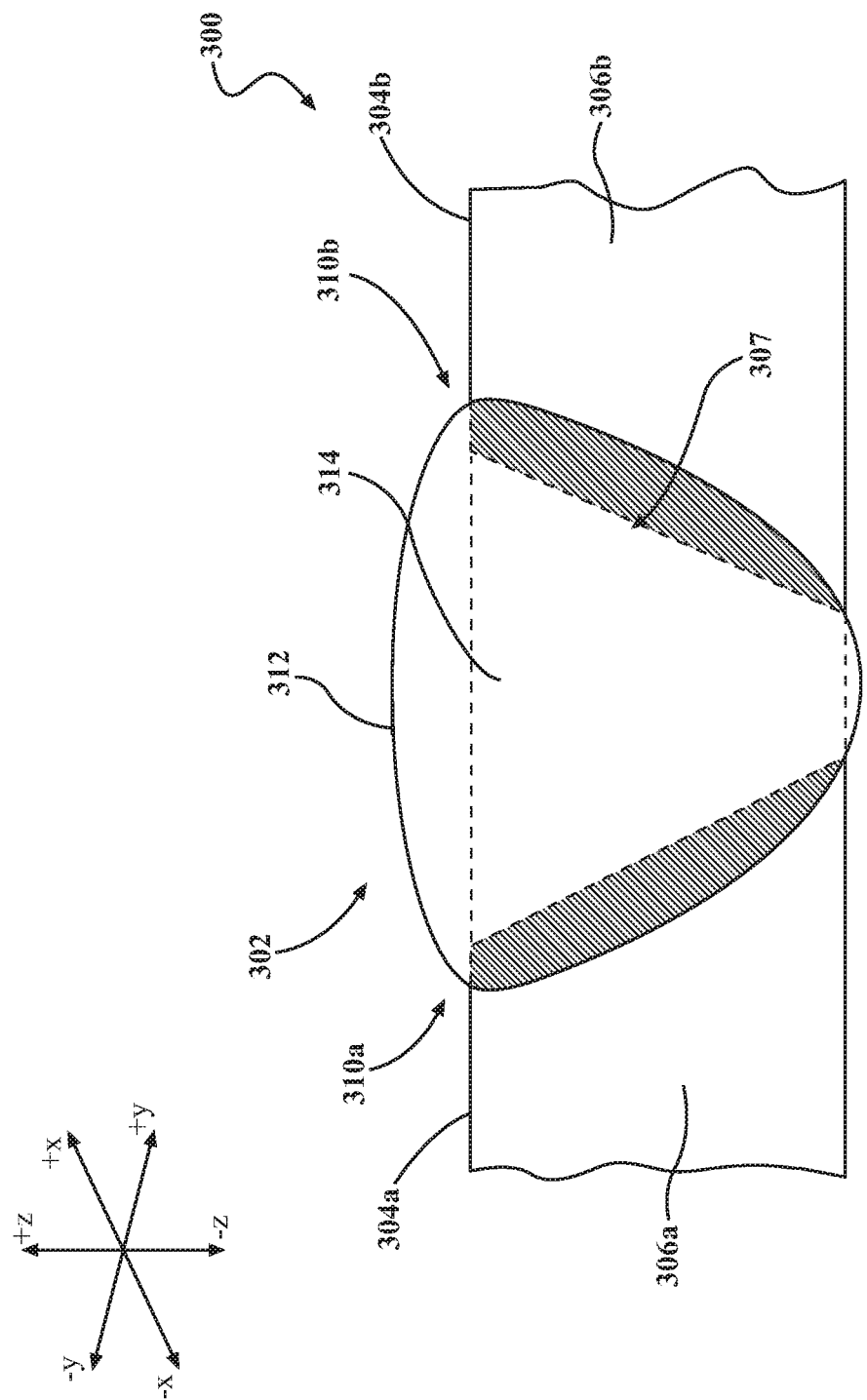
FIG. 3 schematically depicts an illustrative view of a weld bead according to one or more embodiments shown and described herein.

As used herein, the term "system longitudinal direction" refers to the forward-rearward direction of the system (i.e., in the +/−X direction depicted in FIG. 3). The term "system lateral direction" refers to the cross-direction (i.e., in the +/−Y direction depicted in FIG. 3), and is transverse to the longitudinal direction. The term "system vertical direction" refers to the upward-downward direction of the system (i.e., in the +/−Z direction depicted in FIG. 3). As used herein, "upward" or "top" is defined as the positive Z direction of the coordinate axis shown in the drawings. "Downward" or "below" is defined as the negative Z direction of the coordinate axis shown in the drawings. Further, the term "length" is defined as the X direction of the coordinate axis shown in the drawings and the term "width" is defined as the Y direction of the coordinate axis shown in the drawings.

Figure 1:
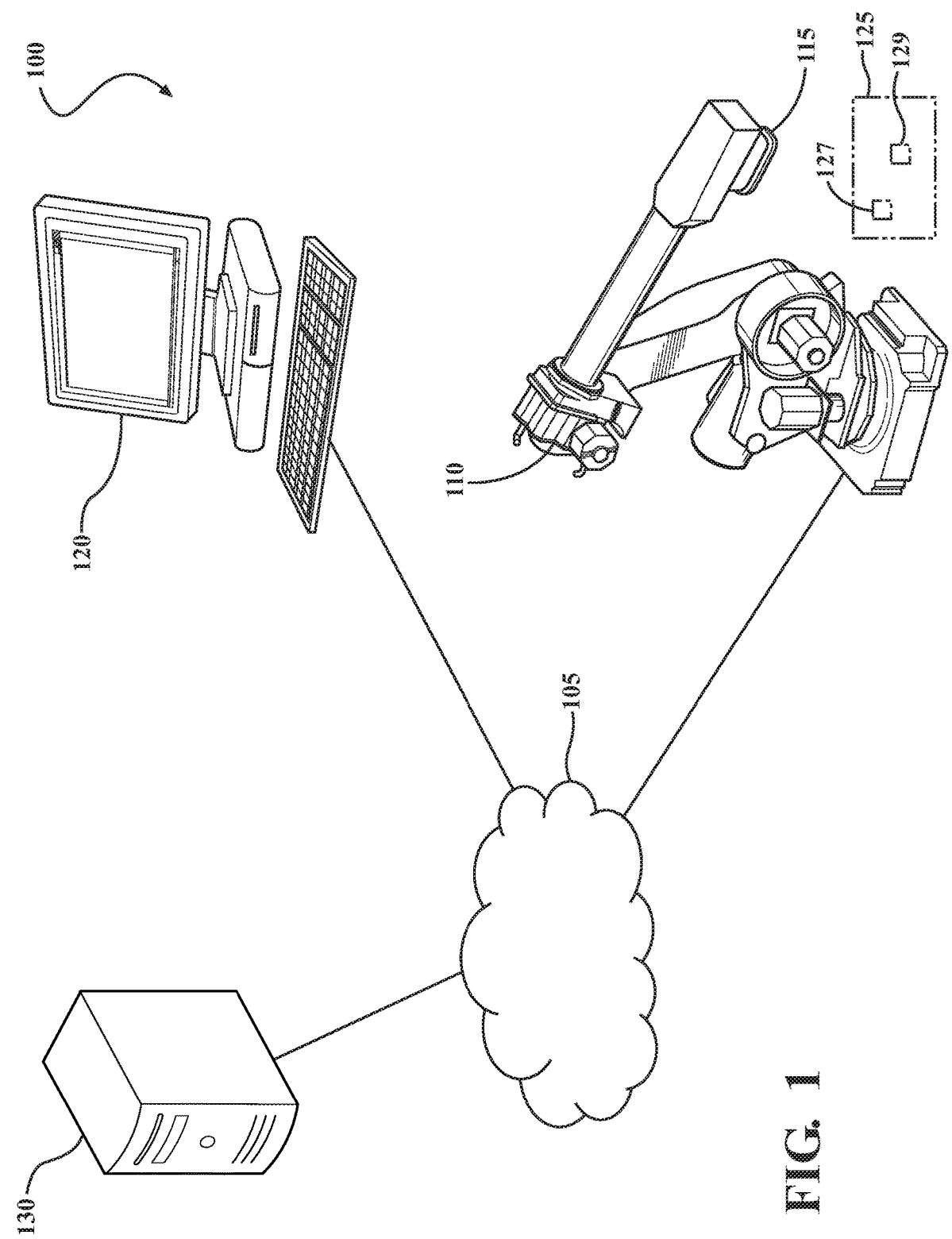
FIG. 1 schematically depicts an illustrative network having components for a system that scans a weld bead and converts the scan into images so to measure the weld bead according to one or more embodiments shown and described herein.

Referring now to the drawings, FIG. 1 depicts an illustrative network 100 having components for a system for scanning a weld bead and analyzing the scanned weld bead to determine whether the weld bead conforms to predetermined quality parameters according to embodiments shown and described herein. As illustrated in FIG. 1, a computer network 105 may include a wide area network (WAN), such as the Internet, a local area network (LAN), a mobile communications network, a public service telephone network (PSTN), a personal area network (PAN), a metropolitan area network (MAN), a virtual private network (VPN), and/or another network. The computer network 105 may generally be configured to electronically connect one or more devices such as computing devices and/or components thereof. Illustrative devices may include, but are not limited to, a robot 110, a user-computing device 120, and a server-computing device 130.

The robot 110 may generally be any robot with one or more computing devices, particularly computing devices that contain hardware for processing data, storing data, and scanning weld beads. Thus, the robot 110 and/or components thereof may perform one or more computing functions, such as receiving data, capturing image data (e.g., scanned images) with a line scanning device 115, processing the scanned images, storing the processed scanned images, and analyzing the processed scanned images for weld quality, as described in greater detail herein. Further, it should be appreciated that the robot 110 and in particular the line scanning device 115 may be configured to scan and/or measure a weld bead of a first part assembly 127 positioned within the parts nest 125. In some embodiments, the first part assembly 127 includes at least one part. In some embodiments, the first part assembly 127 includes at least two parts joined together by the weld bead, as discussed in greater detail herein. Further, it should be appreciated that the part nest 125 and/or the embodiments described herein are not limited to the first part assembly 127 and that there may be a plurality of part assemblies 129 positioned within the part nest 125 having a plurality of welds that may require measuring and/or scanning by the line scanning device 115.

The user-computing device 120 may generally be used as an interface between a user and the other components connected to the computer network 105. Thus, the user-computing device 120 may be used to perform one or more user-facing functions, such as receiving one or more inputs from a user or providing information to the user, as described in greater detail herein. Accordingly, the user-computing device 120 may include at least a display and/or input hardware, as described in greater detail herein. In the event that the server-computing device 130 requires oversight, updating, and/or correction, the user-computing device 120 may be configured to provide the desired oversight, updating, and/or correction. The user-computing device 120 may also be used to input additional data into a corpus of data stored on the server-computing device 130. For example, the user computing device 120 may contain software programming or the like that relates to viewing, interpreting, and/or capturing scanned images of weld beads and other features, as well as software programming that relates analyzing the scanned images of the weld beads and other features.

The server-computing device 130 may receive data from one or more sources, generate data, store data, index data, search data, and/or provide data to the user-computing device 120 and/or the robot 110 (or components thereof). In some embodiments, the server-computing device 130 may employ one or more algorithms that are used for the purposes of analyzing data that is received from the robot 110, such as a plurality of scanned images, as described in greater detail herein. Moreover, the server-computing device 130 may be used to produce data, such as performing one or more analysis functions or storing of analysis data, as described in greater detail herein. It should be appreciated that the computing systems may function with the server-computing device such that the computing systems may perform the one or more analysis functions, storing of analysis data, and/or employ the one or more algorithms.

It should be understood that while the user-computing device 120 is depicted as a personal computer and the server-computing device 130 is depicted as a server, these are non-limiting examples. In some embodiments, any type of computing device (e.g., mobile computing device, personal computer, human machine interface (HMI), server, etc.) may be used for any of these components. Additionally, while each of these computing devices is illustrated in FIG. 1 as a single piece of hardware, this is also merely an example. Each of the user-computing device 120 and the server-computing device 130 may represent a plurality of computers, servers, databases, components, and/or the like.

FIG. 2A schematically depicts illustrative hardware components of the robot 110 that may be used in scanning and analyzing weld beads for weld quality determination. While the components depicted in FIG. 2A are described with respect to the robot 110, it should be understood that similar components may also be used for the user computing device 120 (FIG. 1) and/or the server computing device 130 (FIG. 1) without departing from the scope of the present disclosure. Further, it should be appreciated that the while the components depicted in FIG. 2A are described with respect to the robot 110, it should be understood that similar components may also be used external to the robot 110 and/or the network 100 (FIG. 1).

The robot 110 may include a system component 200 having a non-transitory computer-readable medium for completing the various processes described herein, embodied as hardware, software, and/or firmware, according to embodiments shown and described herein. While in some embodiments the system component 200 may be configured as a general-purpose computer with the requisite hardware, software, and/or firmware, in other embodiments, the system component 200 may also be configured as a special purpose computer designed specifically for performing the functionality described herein. For example, the system component 200 may be a device that is particularly adapted to utilize machine learning algorithms for the purposes of autonomously or semi-autonomously controlling the robot 110 and/or the line scanning device 115. In another example, the system component 200 may be a device that is particularly adapted to utilize algorithms for the purposes of scanning other features of a component part so to offset the line scanning device 115.

Still referring to FIG. 2A, the system component 200 may generally be an onboard robot computing system. In some embodiments, the system component 200 may be a plurality of robot computing systems or a programmable logic controller (PLC).

As also illustrated in FIG. 2A, the system component 200 may include a processing device 204, an I/O hardware 208, a network interface hardware 210, a non-transitory memory component 212, a system interface 214, a data storage device 216, and the line scanning device 115. A local interface 202, such as DeviceNet, Ethernet, and/or the like, may interconnect the various components.

The processing device 204, such as a computer processing unit (CPU), may be the central processing unit of the system component 200, performing calculations and logic operations to execute a program. The processing device 204, alone or in conjunction with the other components, is an illustrative processing device, computing device, processor, or combination thereof. The processing device 204 may include any processing component configured to receive and execute instructions (such as from the data storage device 216 and/or the memory component 212).

The memory component 212 may be configured as a volatile and/or a nonvolatile computer-readable medium and, as such, may include random access memory (including SRAM, DRAM, and/or other types of random access memory), read only memory (ROM), flash memory, registers, compact discs (CD), digital versatile discs (DVD), and/or other types of storage components. The memory component 212 may include one or more programming instructions thereon that, when executed by the processing device 204, cause the processing device 204 to complete various processes, such as the processes described herein with respect to FIG. 10. Still referring to FIG. 2A, the programming instructions stored on the memory component 212 may be embodied as a plurality of software logic modules, where each logic module provides programming instructions for completing one or more tasks, as described in greater detail below with respect to FIG. 2B.

The network interface hardware 210 may include any wired or wireless networking hardware, such as a modem, a LAN port, a wireless fidelity (Wi-Fi) card, WiMax card, mobile communications hardware, and/or other hardware for communicating with other networks and/or devices. For example, the network interface hardware 210 may provide a communications link between the robot 110 and the other components of the network 100 depicted in FIG. 1, including (but not limited to) the server computing device 130.

Still referring to FIG. 2A, the data storage device 216, which may generally be a storage medium, may contain one or more data repositories for storing data that is received and/or generated. The data storage device 216 may be any physical storage medium, including, but not limited to, a hard disk drive (HDD), memory, removable storage, and/or the like. While the data storage device 216 is depicted as a local device, it should be understood that the data storage device 216 may be a remote storage device, such as, for example, a server computing device or the like (e.g., the server computing device 130 of FIG. 1). Illustrative data that may be contained within the data storage device 216 is described below with respect to FIG. 2C. It should be appreciated that the amount of available storage space in the data storage device 216 may be limited due to its location in the system component 200 in some embodiments. As such, it may be necessary to minimize the size of the data stored thereon, as described in greater detail herein.

Still referring to FIG. 2A, the I/O hardware 208 may communicate information between the local interface 202 and one or more other components of the robot 110. For example, the I/O hardware 208 may act as an interface between the system component 200 and other components, such as pneumatic cylinders, proximately sensors, ladder logic for clamps, pneumatic sensors, and proximately sensors, and/or the like. In some embodiments, the I/O hardware 208 may be utilized to transmit one or more commands to the other components of the robot 110.

The system interface 214 may generally provide the system component 200 with an ability to interface with one or more external devices such as, for example, the user computing device 120 and/or the server computing device 130 depicted in FIG. 1. Communication with external devices may occur using various communication ports (not shown). An illustrative communication port may be attached to a communications network.

Still referring to FIG. 2A, the line scanning device 115 may be communicatively coupled to the local interface 202 and coupled to the processing device 204 via the local interface 202. The line scanning device 115 may be any line scanning device, imaging device, sensor, or detector that is suitable for scanning objects to obtain a surface profile. As used herein, the term "line scan", "line scanning", "laser scanner", or "profile scanner" refers to scanning an object to obtain a two-dimensional and/or three dimensional measurement of the surface profile. Any suitable commercially available line scanning device 115, image device, scanning device, and/or the like may be used without departing from the scope of the present disclosure. In some embodiments, the line scanning device 115 may be coupled to one or more other components that provide additional functionality for imaging, such as, for example, one or more sensors.

The line scanning device 115 may include or may be coupled to a sensor head (not shown). The sensor head is not limited by this disclosure and may generally be any device that is configured to measure the surface profile of a target in the X and Z directions along with a height, width, and/or gap on a surface profile such that a surface scan of a weld bead can be properly obtained. In some embodiments, the sensor head may be a fixed device that is not adjustable. In other embodiments, the sensor head may be adjustable, either manually or automatically by the processing device 204, to zoom in on a target, zoom out on a target, and/or the like.

Figure 2B:
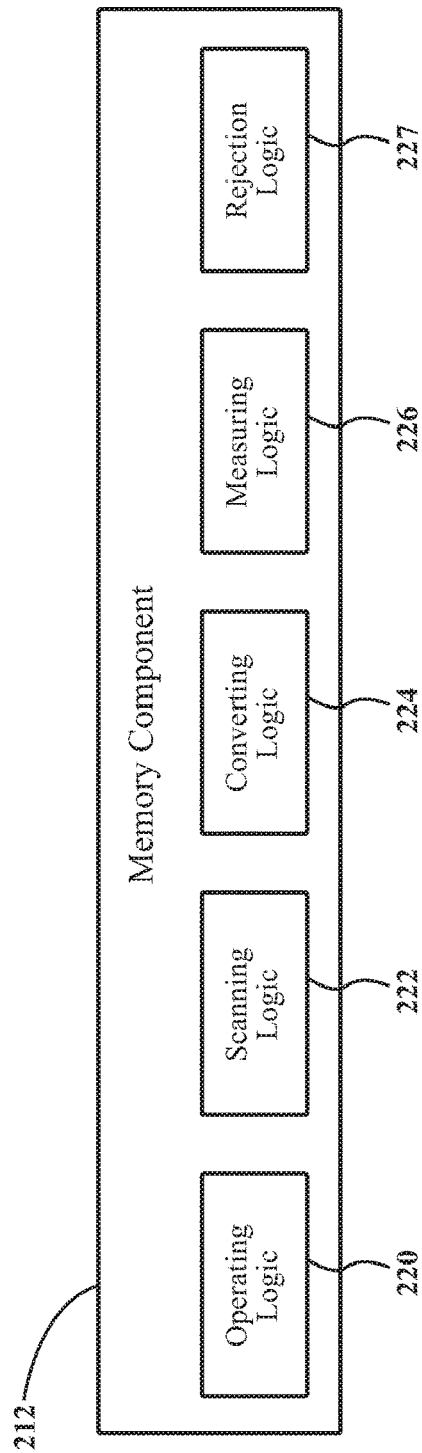
FIG. 2B schematically depicts an illustrative memory component containing illustrative logic components according to one or more embodiments shown and described herein.

With reference to FIG. 2B, in some embodiments, the program instructions contained on the memory component 212 may be embodied as a plurality of software modules, where each module provides programming instructions for completing one or more tasks. For example, FIG. 2B schematically depicts the memory component 212 containing illustrative logic components according to one or more embodiments shown and described herein. As shown in FIG. 2B, the memory component 212 may be configured to store various processing logic, such as, for example, operating logic 220, scanning logic 222, converting logic 224, measuring logic 226, and/or rejection logic 227 (each of which may be embodied as a computer program, firmware, or hardware, as an example). The operating logic 220 may include an operating system and/or other software for managing components of the system component 200 (FIG. 2A). Further, the operating logic 220 may contain one or more software modules for transmitting data, and/or analyzing data.

Still referring to FIG. 2B, the scanning logic 222 may contain one or more software modules for collecting data from one or more sources (e.g. the line scanning device 115, the server computing device 130 depicted in FIG. 1, and/or the like), as described in greater detail herein. The scanning logic 222 may be configured to create and/or process a line scanning profile such that an image captured from the line scanning device 115 (FIG. 2A) into, for example, 3500 slices in which each slice of the image may be converted into a binary number 0-255. As such, each slice is assigned a binary number so that the binary number may be compared to a predetermined threshold such that each slice and the entire weld bead profile may be analyzed accurately and consistently, as discussed herein. The converting logic 224 may contain one or more software modules for converting the slice data, the binary number data, the weld bead profile, and/or the like from the scanning logic 222, such that, for example, a volume data of the weld bead may be determined, as described in greater detail herein.

The converting logic 224 may convert the line scanning profile data, the binary numbers, the slices, and/or the like into a format such that measurements may be taken from the line scanning profile obtained from the line scanning device 115. The converting logic 224 may reside on different computing devices. As an example, one or more of the functionalities and/or components described herein may be provided by the user computing device 120 and/or the server computing device 130, which may be coupled to the memory component 212 via the network 100, such that access to the converting logic 224 may be provided. For example, the processing device 204 (FIG. 2A) may access the converting logic 224 to communicate and retrieve the line scanning data and then use the server computing device 130 and/or the like to manipulate the line scanning profile data. The measuring logic 226 may contain one or more software modules for measuring the line scanning profile data, assigning binary numbers, measuring slices, and/or the like as discussed in greater detail herein. The measuring logic 226 may reside on different computing devices. As an example, one or more of the functionalities and/or components described herein may be provided by the user computing device 120 and/or the server computing device 130, which may be coupled to the memory component 212 via the network 100, such that access to the measuring logic 226 may be provided. For example, the processing device 204 (FIG. 2A) may access the converting logic 224, as discussed above, and the measuring logic 226 to communicate and measure the line scanning profile data and then use the server computing device 130 and/or the like to manipulate the measured line scanning profile data. The rejection logic 227 may contain one or more software modules for determining the weld quality from the measuring logic 226 and comparing the measured values to predetermined parameters and thresholds, and rejecting the weld based on the measurement data that does not conform with the predetermined parameters or meet the minimum thresholds from the measuring logic 226, as described in greater detail herein.

Figure 2C:
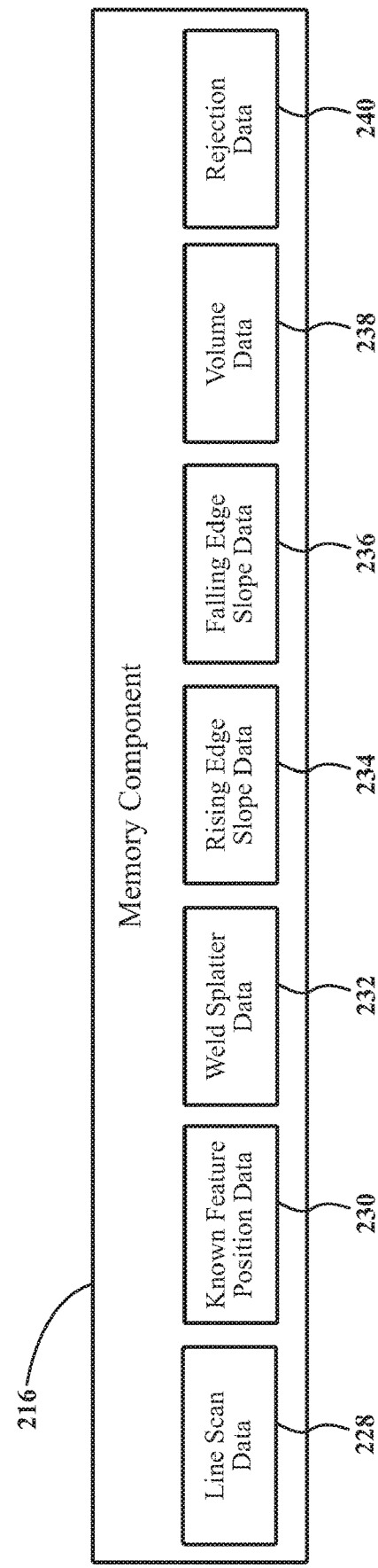
FIG. 2C schematically depicts an illustrative data storage device containing illustrative data components according to one or more embodiments shown and described herein.

FIG. 2C schematically depicts a block diagram of various data contained within a storage device (e.g., the data storage device 216). As shown in FIG. 2C, the data storage device 216 may include, for example, a plurality of stored line scan data 228, such as the surface profile of a plurality of weld beads, as discussed in greater detail herein. It should also be understood that the plurality of stored line scans data 228 may also be data gathered may include a plurality of images of the target objects and/or data of target objects. The plurality of stored line scans data 228 may be received, for example, from the server computing device 130 (FIG. 1) or received from, for example, the line scanning device 115, as discussed herein. It should be appreciated that the plurality of stored line scans data 228 may not be stored permanently, but instead may be stored temporarily such that the data may be extracted therefrom.

The data storage device 216 may further include, for example, a plurality of known features positions data 230 such that the line scanning device 115 offset positon may be obtained based on the known feature positions, as discussed in greater detail herein. In some embodiments, the known features positions data 230 may further include data related to a summed height of at least two parts such that proper positioning or placement of the first part to a second part may be determined. The data storage device 216 further include a weld splatter data 232, a plurality of rising edge slope data 234, a plurality of falling edge slope data 236, a volume of the face data 238, and/or a rejection data 240.

The weld splatter data 232, the rising edge slope data 234, the falling edge slope data 236, and/or the volume of the face data 238 may be received from line scanning device 115 (FIG. 2A) through the scanning logic 222 (FIG. 2B), the converting logic 224 (FIG. 2B), and/or the measuring logic 226 (FIG. 2B). The weld splatter data 232, the rising edge slope data 234, the falling edge slope data 236, and/or the volume of the face data 238 may be captured in real time or may be created, as will be discussed in greater detail herein. In some embodiments, the weld splatter data 232, the rising edge slope data 234, the falling edge slope data 236, and/or the volume of the face data 238 may be captured from a plurality of different weld beads, different components of parts, different abutting surfaces, and/or the like. The weld splatter data 232, the rising edge slope data 234, the falling edge slope data 236, and/or the volume of the face data 238, when captured by the line scanning device 115 (FIG. 2A), are processed by the processing device 204 (FIG. 2A) and/or the memory component 212 (FIG. 2A).

The rejection data 240 includes a plurality of predetermined acceptable parameters and thresholds that are used in comparisons with the weld splatter data 232, the rising edge slope data 234, the falling edge slope data 236, and/or the volume of the face data 238 to determine if the weld bead has a satisfactorily weld quality. In some embodiments, the rejection data 240 may be preprogrammed parameters that are added, changed, modified, amended, and the like through devices such as the user-computing device 120, server computing device 130, and the like. In other embodiments, the rejection data 240 is machine learned data. In yet other embodiments, the rejection data 240 includes a plurality of predetermined acceptable parameters and thresholds that are used in comparisons with known features positions data 230 to determine whether the parts are positioned or their placement with respect to one another is proper such that the weld bead has a satisfactorily weld quality for the now combined part.

It should be understood that the components illustrated in FIGS. 2A-2C are merely illustrative and are not intended to limit the scope of this disclosure. More specifically, while the components in FIGS. 2A-2C are illustrated as residing within the system component 200 of the robot 110, this is a non-limiting example. In some embodiments, one or more of the components may reside external to the system component 200 and/or the robot 110, such as in a programmable logic controller (PLC) remote from the robot 100, and/or other components. Similarly, as previously described herein, while FIGS. 2A-2C are directed to the system component 200 of the robot 110, other components such as the user computing device 120 and the server computing device 130 may include similar hardware, software, and/or firmware.

As mentioned above, the various components described with respect to FIGS. 2A-2C may be used to carry out one or more processes and/or produce data that can be completed by less powerful processors and/or processors that require fewer resources, such as, for example, robot-based computing devices.

Now referring to FIG. 3 a weld 300 including a weld bead 302 will now be described. The weld bead 302 may be any raised weld, at least partially in the system vertical direction (i.e., in the +/−Z direction) away from two work surfaces 304a, 304b. Generally, the raised weld bead 302 is positioned along a longitudinal length in the system longitudinal direction (i.e., in the +/−X direction), between or on two abutting surfaces, at a joint 307 of the two work surfaces 304, 304b where each of the two work surfaces may each be disposed on one of at least two part components 306a, 306b, as discussed herein. It should be appreciated that the work surface 304a may be on one side of the abutting surfaces 410 (FIG. 4A) of the at least two part components 306a, 306b and the work surface 304b may be on the other side of the abutting surface 410 (FIG. 4A) of the at least two part components 306a, 306b. As such, the abutting surface 410 (FIG. 4A) of the at least two part components 306a, 306b may extend longitudinally beyond the weld bead 302.

The work surface 304a abuts the weld bead 302 at a region generally known as a toe region 310a of the weld bead 302. Further, work surface 304b abuts the weld bead 302 at a region generally known as a toe region 310b of the weld bead 302. A face 312 of the weld bead 302 extends a length in the system longitudinal direction (i.e., in the +/−X direction) between the toe region 310a and the toe region 310b. The face 312 generally extends a length in the system longitudinal direction (i.e., in the +/−X direction) along at least a portion of the joint 307 of the abutting surfaces 410. Further, the face 312 raises vertically in the system vertical direction (i.e., in the in the +/−Z direction), away from the work surfaces 304a, 304b and generally is curvilinear in shape with the peak, or the most vertical portion in the +Z direction of the face 312, near the joint 308. Disposed below the face 312, generally into the joint 307, is a filler 314 of the weld bead 302. Generally, the filler 314 is the strength of the weld bead 302. It should be appreciated that because the face 312 is disposed above the filler 314 in the system vertical direction (i.e., in the +/−Z direction), that the shape of the face 312 and the height has a direct correlation to the shape and height of the filler 314.

Now referring to FIGS. 3-7C, a line scan profile 400 of the weld bead 302 will now be described. The line scanning device 115 (FIG. 2), typically mounted to the robot 110 (FIG. 2) emits a laser beam configured to be moved back and forth along the length of the weld bead 302 of the first part assembly 127 (FIG. 1) positioned within the parts nest 125 (FIG. 1). As such, the laser of the line scanning device 115 (FIG. 2) generally begins one scan at an edge of the work surface 304a, typically before the joint 307 of the abutting surface 410 and moves across the weld bead 302 until the laser beams reaches the other side of the abutting surface 410, at an edge of the work surface 304b, which is on the opposite side of the weld bead 302. The line scanning device 115 may perform a plurality of these scans for a given length of the weld bead 302, for a plurality of weld beads, and/or a combination thereof.

During each scan of the weld bead 302, a plurality of positional data points are collected. These data points are collected as (X, Y, Z) coordinates with X representing a length of the weld bead 302 in the system longitudinal direction (i.e., in the +/−X direction), Y representing the width direction of the weld bead 302 the system lateral direction (i.e., in the +/−Y direction), and Z representing the height of the weld bead 302 the system vertical direction (i.e., in the +/−Z direction). These positional data points are translated into a usable format (i.e. by the memory component 212 of FIG. 2B) so to establish the line scan profile 400, as shown in FIGS. 4A-4D. The line scan profile 400 is established for every weld bead 302, which is preprogrammed as discussed herein. The system establishes the line scan profile 400, from the rest of the line scan data, by determining which part of the scan is the weld bead 302, indicated by the boundary lines 401a, 401b. That is, the system determines whether the weld bead 302 is placed on the joint 307 (FIG. 3) by determining which raised portion is the weld bead 302 as opposed to which section of the line scan profile are not the weld bead to be analyzed (i.e. the at least two parts components 306a, 306b, other weld beads, and/or the like). It should be appreciated that the boundary lines 401a, 401b may be a preliminary predefined parameter to ensure that the weld bead 302 is positioned correctly on the at least two part components 306a, 306b. Further, the system recognizes that any other raised area, in the system vertical direction (i.e., in the +/−Z direction), outside of the boundary lines 401a, 401b may cause the part to be rejected for a number of reasons including unwanted weld splatter (FIGS. 8A-8B), as discussed in greater detail herein.

Figure 4A:
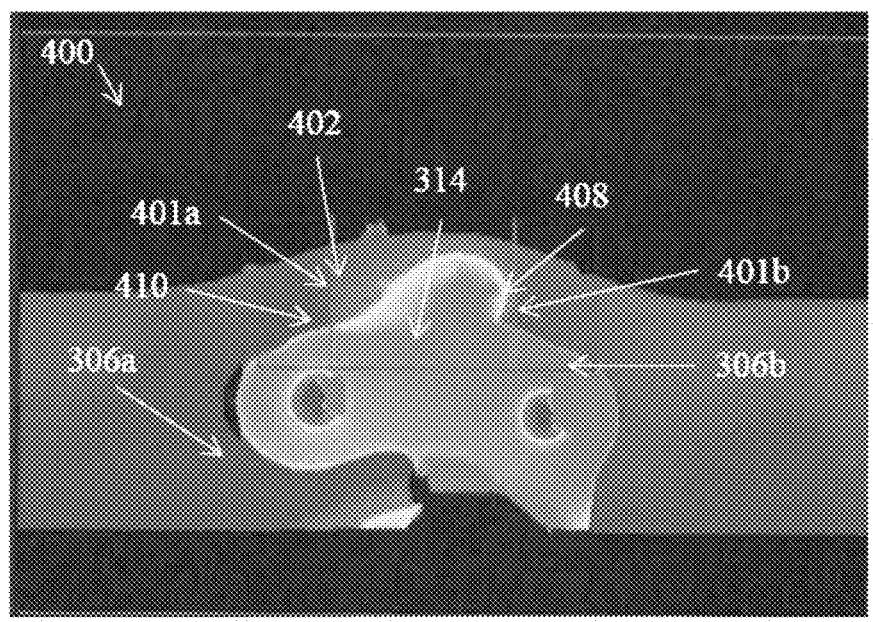
FIG. 4A schematically depicts an illustrative top view of a line scan profile of the weld bead of FIG. 3 according to one or more embodiments shown and described herein.
Figure 4A:
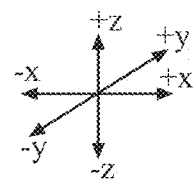
Figure 4B:
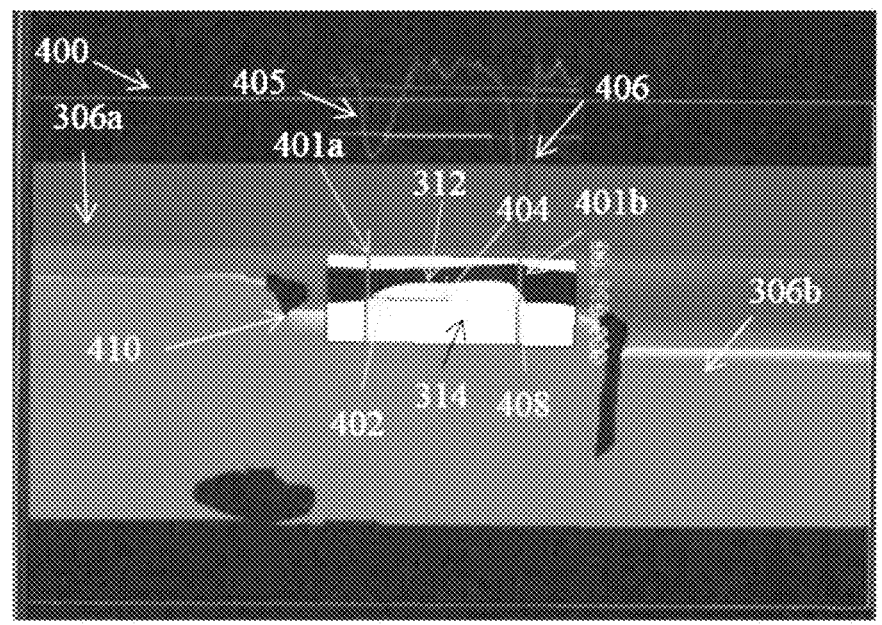
FIG. 4B schematically depicts an illustrative line scan profile view of the weld bead of FIG. 3 according to one or more embodiments shown and described herein.
Figure 4B:
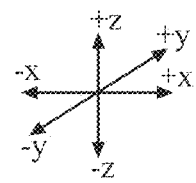
Figure 4C:
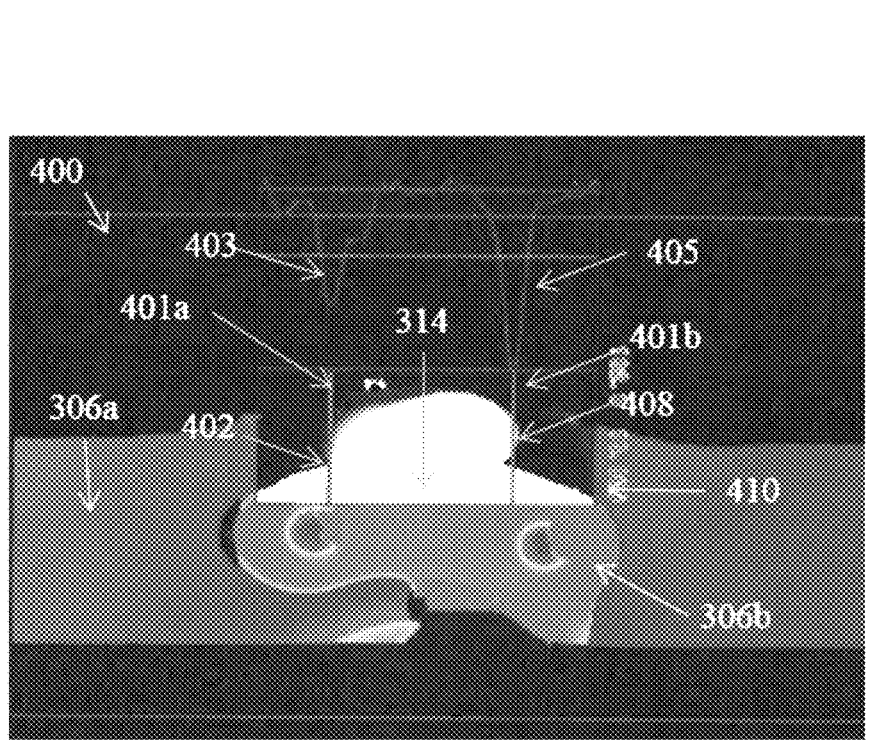
FIG. 4C schematically depicts an illustrative top view of the line scan profile of FIG. 4A according to one or more embodiments shown and described herein.
Figure 4D:
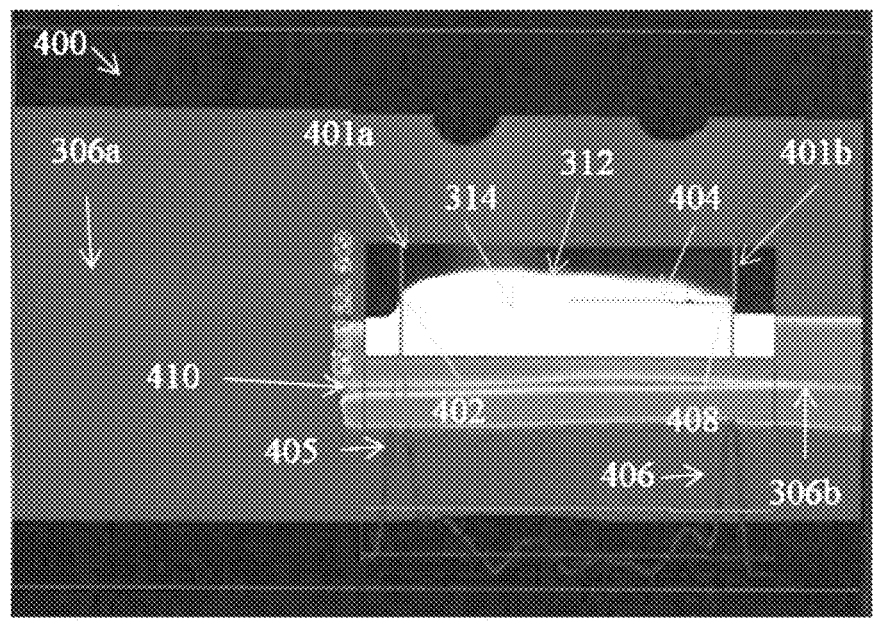
FIG. 4D schematically depicts an illustrative zoomed in line scan profile of FIG. 4B according to one or more embodiments shown and described herein.

With reference to FIGS. 4A and 4C, the line scan profile 400 has been created and the weld bead 302 has been identified, disposed between the boundary lines 401a, 401b. As such, the line scan profile 400 may be analyzed so to determine whether the weld bead 302 meets a plurality of predetermined parameters, such as the length of the weld bead, the volume of the weld bead, and the height that the weld bead extends from the surface of the two abutting surfaces, as discussed in detail herein. Further, the system, as shown in FIGS. 4A and 4C, is configured to determine a rising edge 402 and a falling edge 408 of the weld bead 302 from the line scan profile 400, generally beginning and ending at the boundary lines 401a, 401b, respectfully, and graphically illustrated as peaks 405, 406. The system may determine, with reference to FIGS. 4B and 4D, how large, or how much of a slope of the rising edge 402 and how fast, or how much is a slope of the falling edge 408 by determining the width of the peaks 405, 406 as the width of the peaks correspond to the slope of the edges 402, 408. Further, the system may be configured to determine the vertical height 404 of the rising edge 402 and the falling edge 408 taken from the abutting surfaces, in the system vertical direction (i.e., in the +/−Z direction).

Figure 5A:
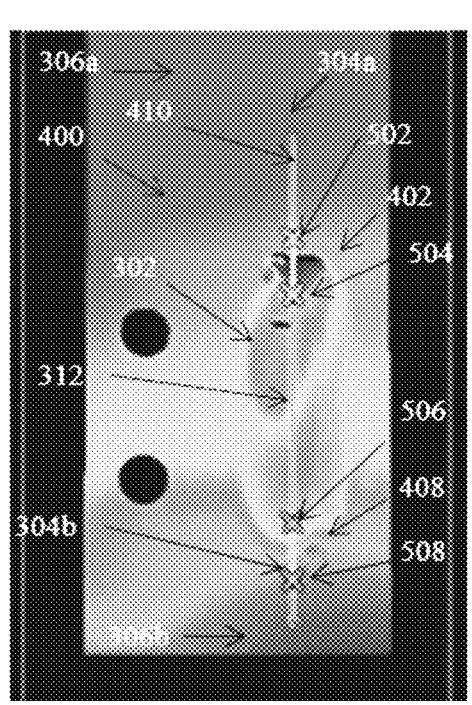
FIG. 5A schematically depicts an illustrative top view of the line scan profile of the weld bead of FIG. 4A according to one or more embodiments shown and described herein.
Figure 5A:
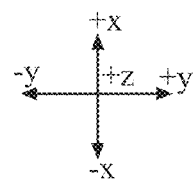
Figure 5B:
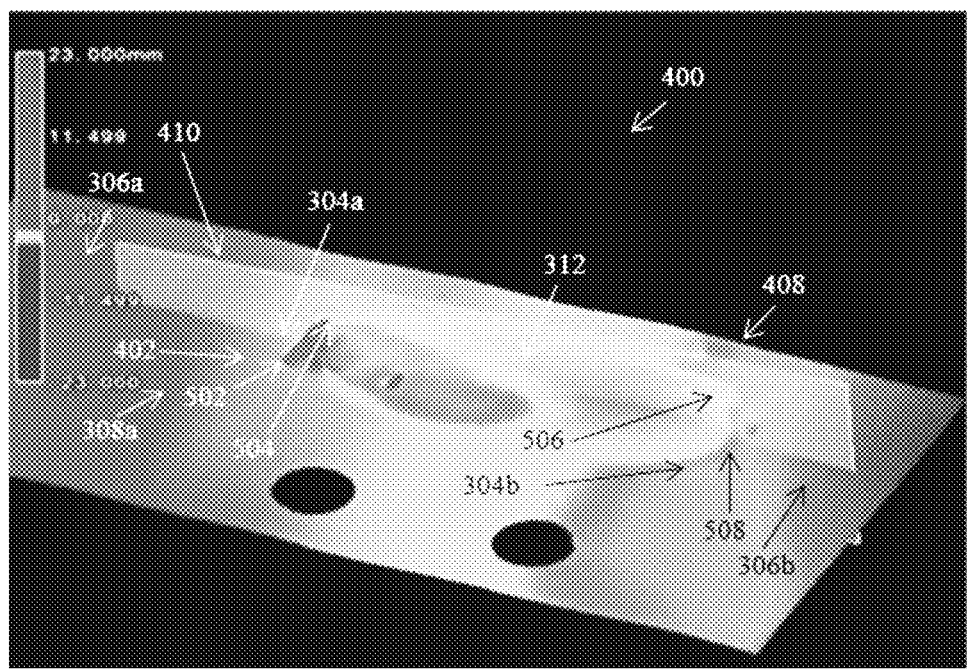
FIG. 5B schematically depicts an illustrative perspective view of the line scan profile of the weld bead of FIG. 4A according to one or more embodiments shown and described herein.
Figure 5B:
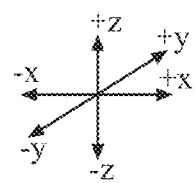

As best seen in FIGS. 5A-5B, the system is configured to determine the height of the rising edge 402 and the slope of the falling edge 408 in the system vertical direction (i.e., in the +/−Z direction), and, in some embodiments, may determine the slope of the rising edge 402 and the falling edge 408. As such, the height is determined using at least two points in each the rising and the falling edge 402, 408. With reference to the rising edge 402, the slope may upward (i.e., in the +Z direction) with reference from the work surface 304a, or in a direction away from the work surface 304a of one of the at least two part components 306a. A first measuring point 502 of the rising edge 402 is where the rising edge begins, at the work surface 304a. The first measuring point 502 may be in the toe region 310a of the weld bead 302. A second measuring point 504 of the rising edge 402 is where the rising edge 402 begins to flatten, or finish, into the face 312 of the weld bead 302. The face 312 continues in the system longitudinal direction (i.e., in the +/−X direction) along at least a portion of the joint 307 until a first measuring point 506 of the falling edge 408. The first measuring point 506 of the falling edge 408 begins where the falling edge 408 begins to slope in the downward (i.e., in the −Z direction), towards the work surface 304b of one of the at least two part components 306b. The falling edge 408 continues to slope down towards the work surface 304b. A second measuring point 508 of the falling edge 408 is where the falling edge makes contact with the work surface 304b of the one of the at least two part components 306b. That is, the falling edge 408 may end its slope in the toe region 310b of the weld bead 302.

Figure 5C:
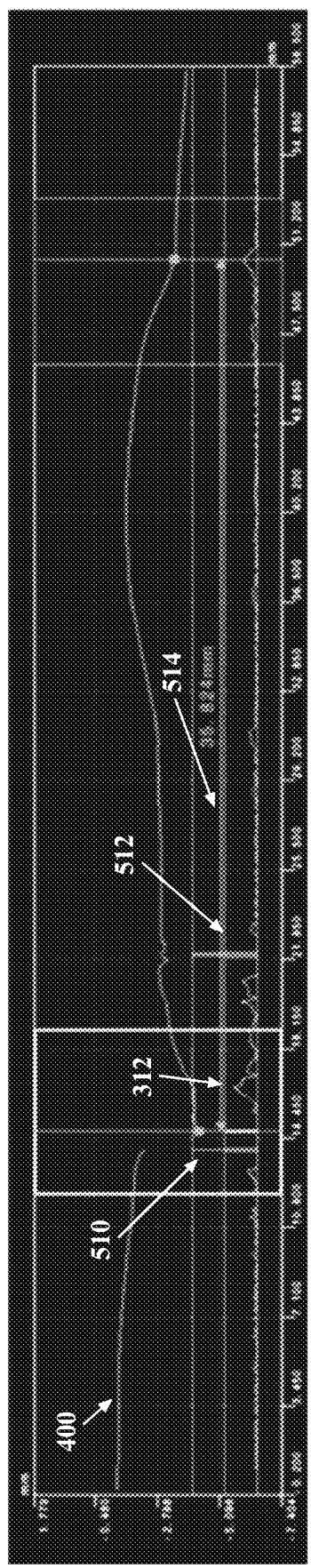
FIG. 5C schematically depicts a graphical representation of the line scan profile of the weld bead of FIG. 4A according to one or more embodiments shown and described herein.

With reference to FIG. 5C, the data from these measuring points 502, 504, 506, 508 may be analyzed to determine the height in the system vertical direction (i.e., in the +/−Z direction), and, in some embodiments, the slopes of each edge 402, 408. The slope of the rising edge 402 may be determined from the graphical representation of the slope, illustrated as a first spike 510. The slope of the falling edge 408 may be determined from the graphical representation of the slope, illustrated as a second spike 512. The width of the first spike 510 and the second spike 512 correlate to the slope of the rising edge 402 and the falling edge 408 respectfully. It should be appreciated that the slopes may indicate the angle, trajectory, and/or the like of the weld bead 302 from the work surface 304a to the face 312 and from the face 312 to the work surface 304b. It should also be appreciated the system may be configured to determine whether the slopes of the rising edge 402 and/or the falling edge 408 are within predefined parameters. As such, the height and/or slopes of the edges 402, 408 may be used to determine the quality of the weld bead 302, as discussed in greater detail herein. For instance, if the height is not sufficient, then the weld bead may lack proper filler 314. Another example is that the slopes of the rising and the falling edges 402, 408 are at a sufficient angle, then the face 312 of the weld bead 302 will be raised from the two work surfaces 304a, 304b such that there is a sufficient amount of filler 314 in the weld bead 302 to properly join the at least two parts components 306a, 306b.

Figure 6A:
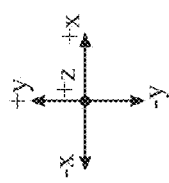
FIG. 6A schematically depicts an illustrative top view of the line scan showing a height measurement of the weld bead of FIG. 4A according to one or more embodiments shown and described herein.
Figure 6A:
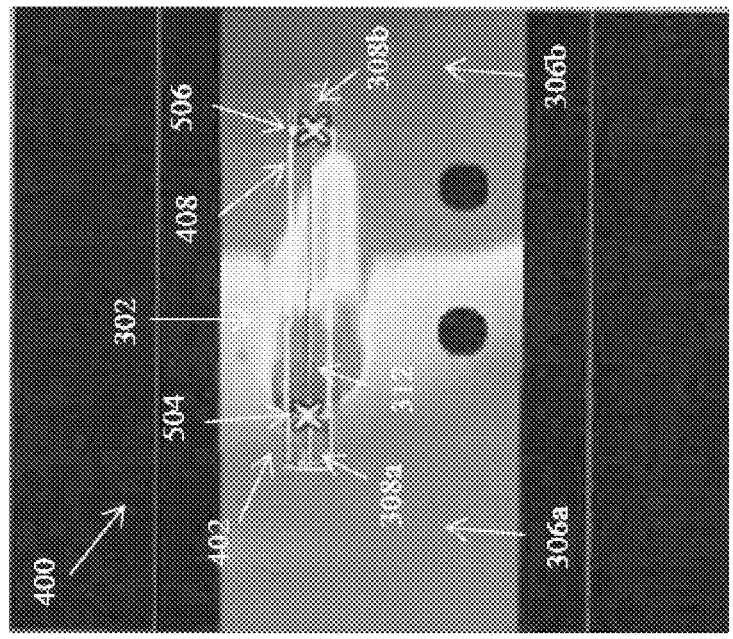

Now referring to FIG. 6A, the system is also configured to determine the volume of the weld bead 302. The volume of the weld bead 302 may be determined based on the vertical height 404 (FIGS. 4B, 4D) of the face 312 of the weld bead 302 in the system vertical direction (i.e., in the +/−Z direction). Similar to the measuring points for determining the slope, the height of the face 312 using the measuring points 504. 506 to determine the height of the face 312. As such, the measuring points 504, 506 provide data such that the system is configured to analyze and determine the vertical height 404 (FIGS. 4B, 4D) of the face 312 of the weld bead 302 in the system vertical direction (i.e., in the +/−Z direction), away from the work surfaces 308a, 308b. Further, as discussed above, the measuring points 504, 506 provide the length of the face 312.

Figure 6B:
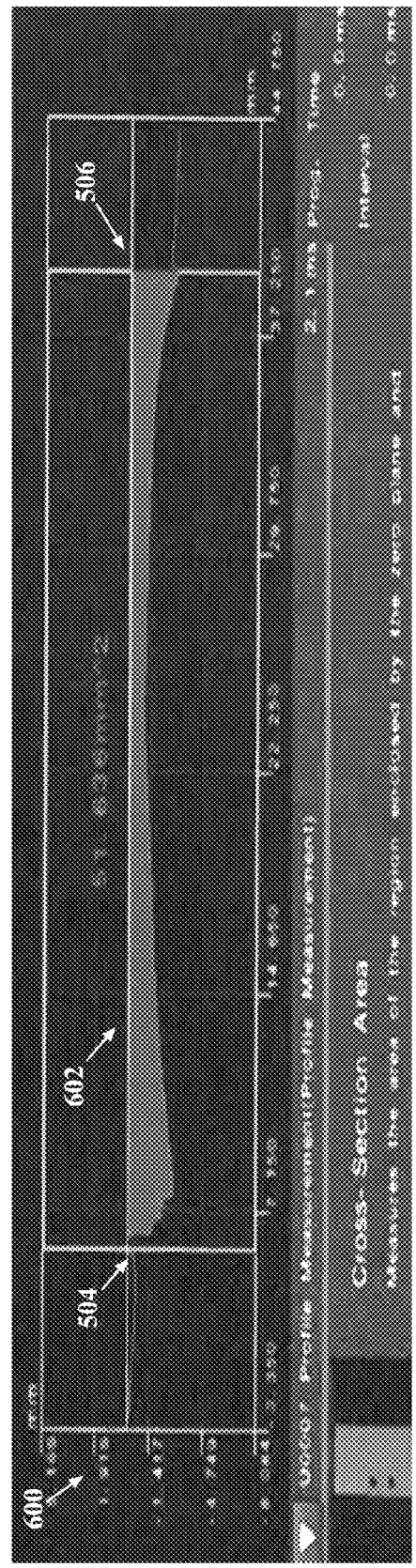
FIG. 6B schematically depicts a graphical representation of a cross sectional volume of the line scan profile of FIG. 4A according to one or more embodiments shown and described herein.

With reference to FIG. 6B, a graphical representation 600 of a volume 602 of the weld bead 302 is depicted. Once the height of the face 312 of the weld bead 302 is established, a cross sectional volume 602 of the weld bead 302 may be determined. That is, the cross section area of the weld bead 302 has to meet a predetermined minimum threshold between the measuring points 504, 506. The cross sectional volume is determined by the system such that the volume of the filler 314 (FIG. 3) and the face 312 of the weld bead 302 is sufficient to meet predetermined threshold above known weld failures.

Figure 7A:
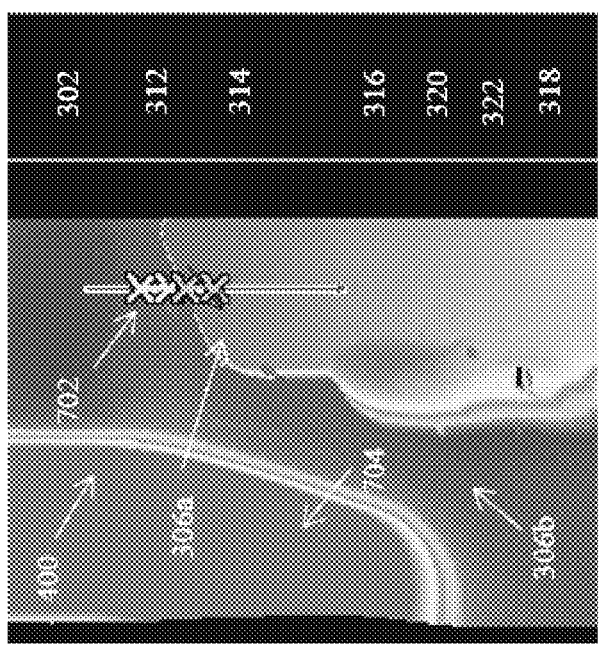
FIG. 7A schematically depicts an illustrative top view of the line scan profile showing a height measurement of a raised surface according to one or more embodiments.
Figure 7B:
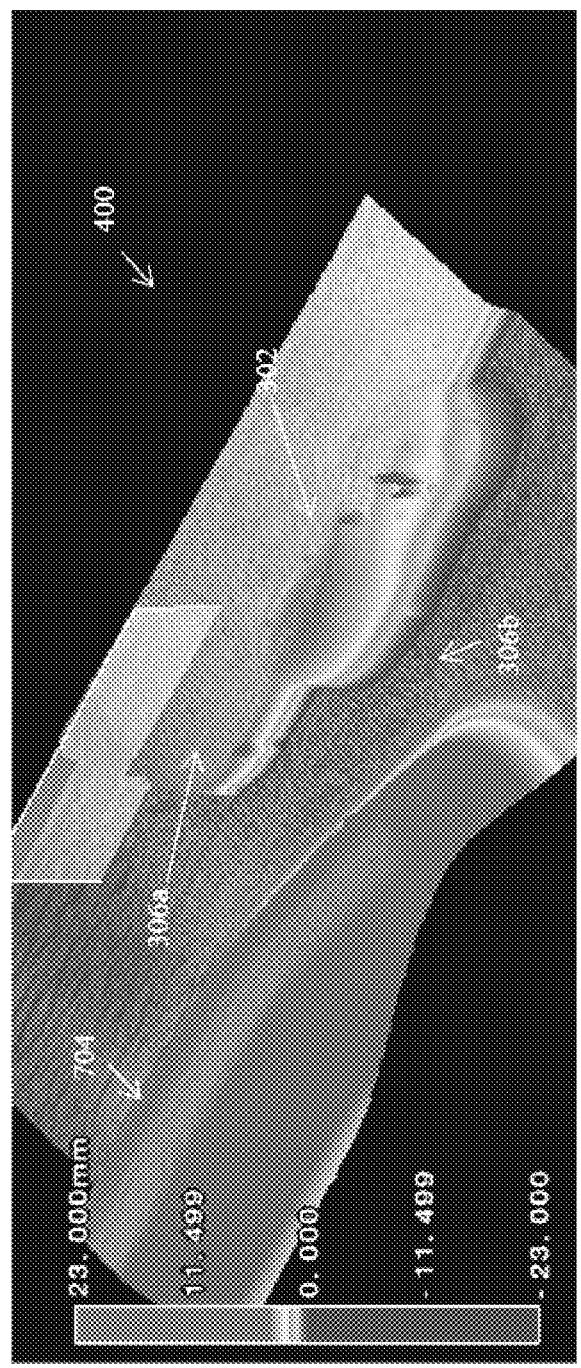
FIG. 7B schematically depicts an illustrative perspective view of the line scan profile showing the height measurement of the raised surface of FIG. 7A according to one or more embodiments.

With reference to FIG. 7A-7B, the system is configured to measure any raised, or lifted, surface, for example, weld expulsion (discussed in greater detail with respect to FIG. 8A-8B), a component with reference to a base portion in the system vertical direction (i.e., in the +/−Z direction), such as one of the at least two part components 306b, and/or the like. In a similar manner to FIGS. 5A-5B, the system may determine the height of any raised component in the system vertical direction (i.e., in the +/−Z direction) using a plurality of measuring points 702. As illustrated, the line scan profile 400 may include other raised surfaces 704 in addition to the weld bead 302. The system may be configured to determine from the line scan, or a snap shot, the height of any component, such as one of the at least two part components 306a from the other one of the at least two part components 306b, the height of the raised surface 704 from the one of the at least two part components 306b, and/or the like. As such, the system may be configured with predetermined heights for components where the system will sum the height of the at least two parts components 306a, 306b and compare the summed value to the threshold amount.

Figure 7C:
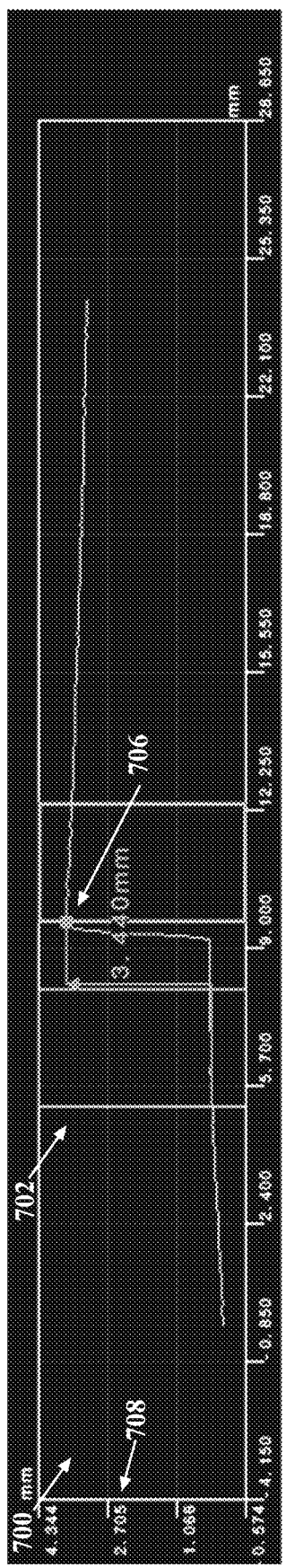
FIG. 7C schematically depicts a graphical representation of the line scan profile of the raised surfaces of FIG. 7A according to one or more embodiments shown and described herein.

With reference to FIG. 7C, a graphical representation 700 of the summed value 706 of the raised surfaces is depicted. The comparison is graphically illustrated in FIG. 7C. The summed value may be determined from the plurality of measuring points 702. As such, the height of the component or the summed value 706 is compared to a predetermined value 708 in order to establish whether the height of the component in the system vertical direction (i.e., in the +/−Z direction) is proper. It should be appreciated that determining the height of the components allows the system to determine whether the components are properly welded together, whether there is additional weld or other foreign material in the line scan, and/or the like.

Figure 8A:
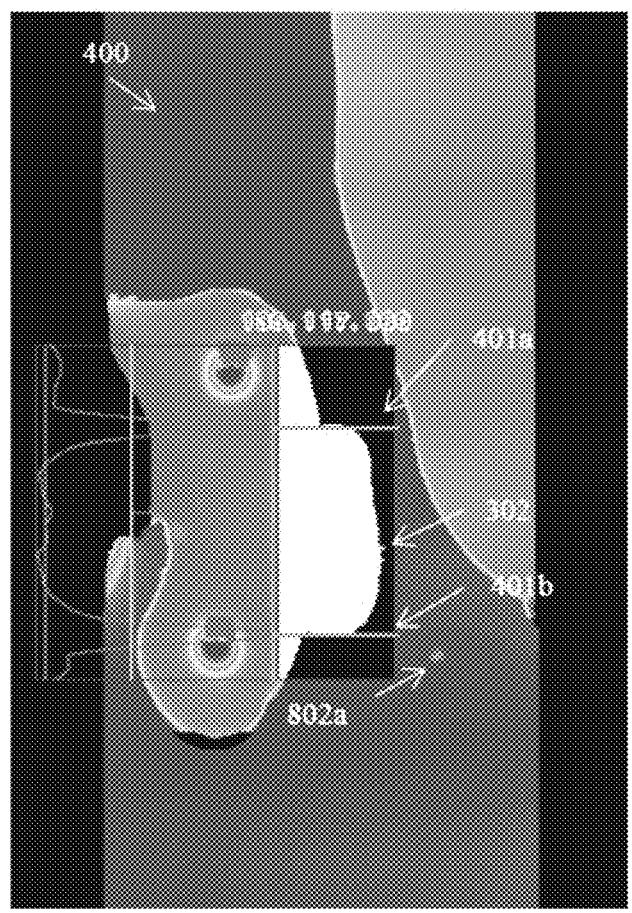
FIG. 8A schematically depicts an illustrative top view of the line scan profile showing a weld spike according to one or more embodiments.
Figure 8B:
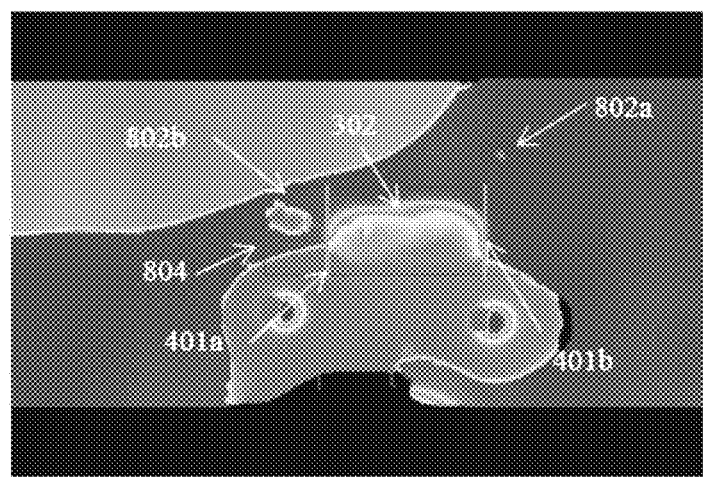
FIG. 8B schematically depicts an illustrative top view of the line scan profile showing a plurality of weld spikes according to one or more embodiments.

With reference to FIGS. 8A-8B, the system is configured to detect raised features outside of areas where the system expects a raised feature to be positioned in the system vertical direction (i.e., in the +/−Z direction). The system uses feature positioning, in which offsets may be used, to ensure that the line scan aligns with the proper weld bead and/or part component. As such, any features that are raised in the system vertical direction (i.e., in the +/−Z direction), are detected by the system. For instance, weld expulsion that causes a plurality of weld spikes 802a, 802b, or weld splatter, to be welded to the surface of the at least two part components 306a, 306b may be detected in the line scan profile 400. It is complemented that these plurality of weld spikes 802a, 802b may be subjected to another set of predetermined parameters such as location, height, and/or the like, in order for the system to determine whether or not to ignore each one or the plurality of weld spikes 802 or reject the part component due to at least one of the weld spikes 802 being outside of the predetermined parameters.

For example, in FIG. 8A, the plurality of weld spikes are located away from the weld bead 302. As such, the predefined parameters may not allow the system to ignore the weld spikes 802a in this location and therefore would reject this part component. On the other hand, for example, in FIG. 8B, the plurality of weld spikes 802b are located near the weld bead 302. As such, the system may have predefined parameters to ignore any raised features, illustrated without limitation as being within the box 804, such that it is expected for those raised features to occur frequently in this area or that a raised feature here does not, for example, impact future welds or part matchup.

Figure 9B:
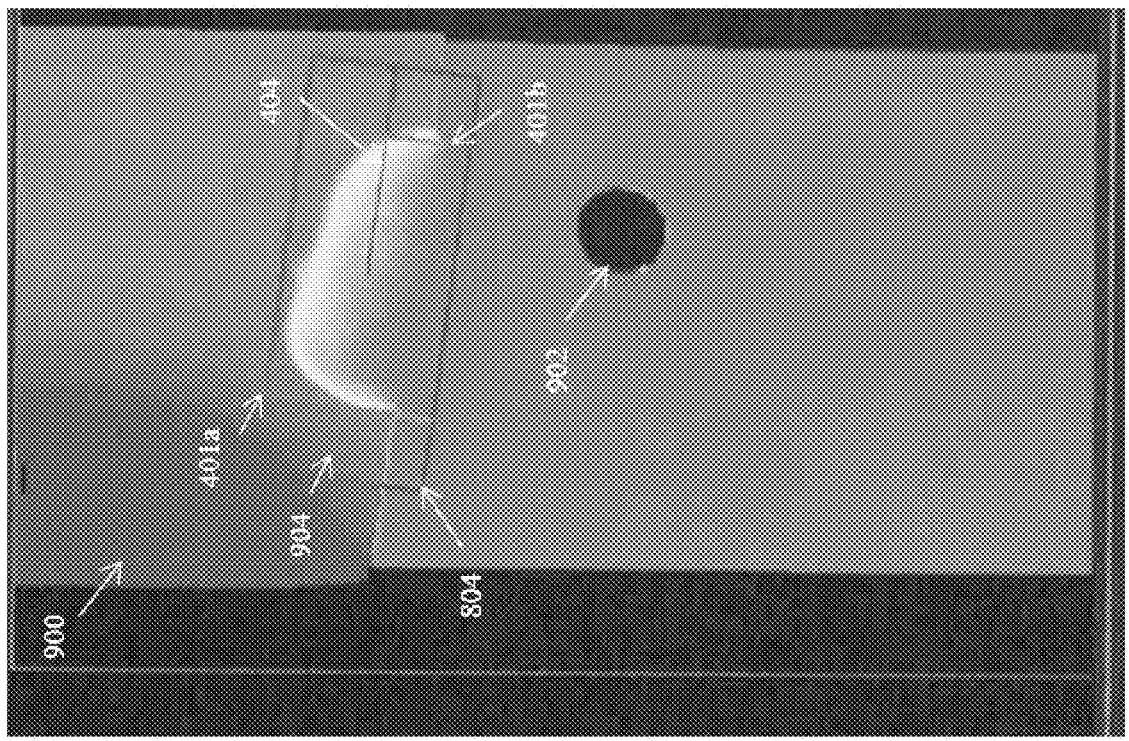
FIG. 9B schematically depicts an illustrative top view of the line scan profile showing an offset feature of the weld bead according to one or more embodiments.
Figure 9A:
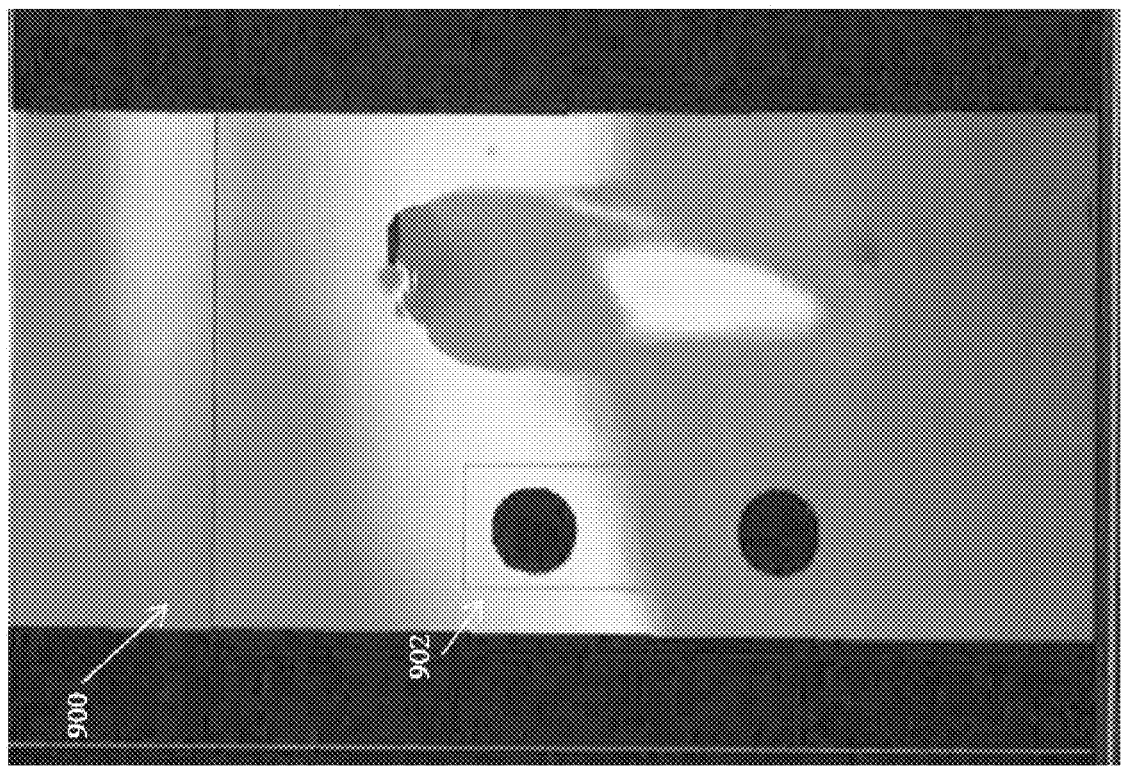
FIG. 9A schematically depicts an illustrative top view of the line scan profile showing an offset feature according to one or more embodiments.

With reference to FIGS. 9A-9B, the system is configured to take an initial line scan 900 to locate features, such as the holes 902 within the part and a predicted weld bead location 904 so to adjust or offset before the scanning for the line scan profile 400 is started. As such, this ensures that the line scan profile 400 matches every weld bead preprogrammed in order, as discussed herein.

Figure 10:
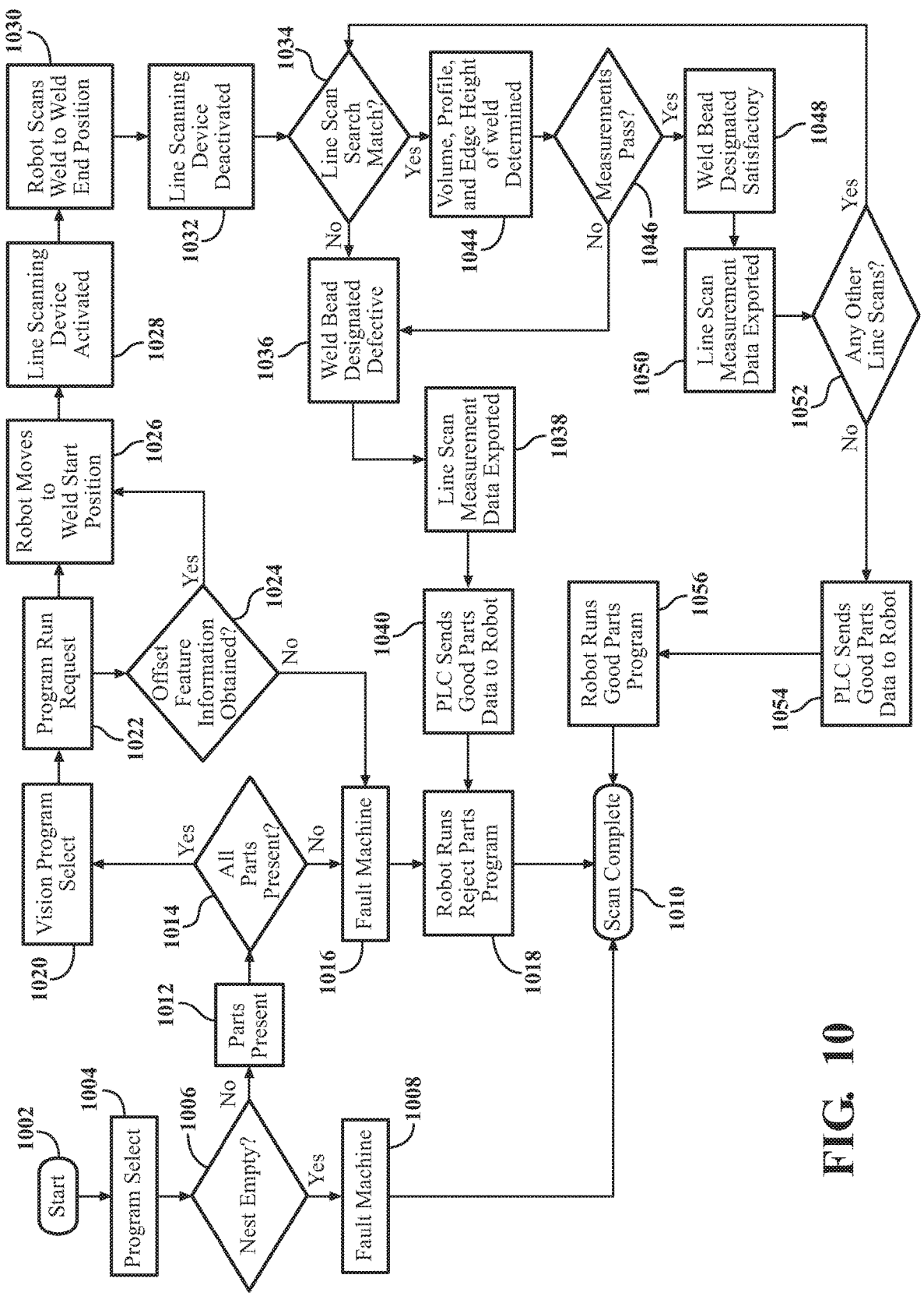
FIG. 10 depicts a flow diagram of an illustrative method of generating and analyzing the line scan profile according to one or more embodiments shown and described herein.

FIG. 10 schematically depicts a flow diagram of an illustrative method 1000 of an operation of the system configured to determine whether the weld bead 302 is proper. The operation begins, at block 1002, waiting for the program select, at block 1004. The system then determines if a plurality of nests for the part components are empty, at block 1006. The nests may be determined to be empty if proximately switches, laser switches, and/or the like do not recognize part components are present within the plurality of nests. If the determination is that the plurality of nests are empty, then the machine is faulted, at block 1008, and the scan complete is initiated, at block 1010.

On the other hand, if the plurality of nests are determined to not be empty and parts are present, at block 1012, then the system determines if all the part components which are required are present in the plurality of nests, at block 1014. The part present may be determined by a plurality of proximately switches, laser switches, and/or the like from with the plurality of nests or external to the plurality of the nests. If the system determines that not all parts are present, the system faults the machine, at block 1016. The machine fault, at block 1016, causes the system to execute a reject parts program and the robot may execute the program such that the parts may be removed from the plurality of nests by the robot and discarded into a reject parts area, at block 1018. The reject parts program may be any predetermined program using automation to remove parts rejected by the system. After the reject parts program, at block 1018, is complete, the scan complete is initialized, at block 1010.

If the all parts present is achieved in block 1014, the system next selects the vision program, at block 1020, and the program run request is initiated, at block 1022, where the line scanning device 115 (FIG. 2A) begins to scan the part components features so to determine what offset, if any, is required to align the line scanning device 115 (FIG. 2A) to the at least two part components 306*a*, 306*b* (FIG. 3) at the weld bead 302 (FIG. 3). If the offset feature information is not obtained by the system then the machine is faulted, at block 1016, the reject parts program may be executed, at block 1018, and the scan complete may be initialized, at block 1010.

On the other hand, if the offset feature information is obtained by the system, at block 1024, then the robot may move to the weld bead 302 (FIG. 3) start position, at block 1026. The line scanning device 115 (FIG. 2A) is activated, at block 1028, and the robot moves in a direction such that the line scanning device (FIG. 2A) may scan the weld bead 302 (FIG. 3) to the weld end position, at block 1030, where the line scanning device is then deactivated, at block 1032, so to create the line scan profile 400.

The line scan profile 400 is then compared to a preliminary predefined parameters, at block 1034, in order to determine whether the line scan profile 400 is a match to the predefined parameters. Example preliminary predefined parameters may be a location of weld bead 302, any raised surfaces outside of a predefined area, the weld bead start and end points, whether the weld bead 302 is between the boundary lines 401*a*, 401*b*, and/or the like. If the line scan profile 400 of the weld bead 302 (FIG. 3) does not match these preliminary predefined parameters, then the weld bead 302 (FIG. 3) is designated as defective, at block 1036, the line scan profile 400 measurement data is exported, at block 1038, a reject parts data program may be initiated by the PLC, at block 1040, such that the robot may execute the program, physically removing the parts from the plurality of nests and discarding the parts into a reject parts area, at block 1018. The reject parts data program may be any predetermined program using the robot (i.e. automation) to physically remove parts rejected by the system. After the reject parts program, at block 1018 is complete, the scan complete is initialized, at block 1010.

On the other hand, if the line scan profile 400 of the weld bead 302 (FIG. 3) matches the preliminary predefined parameters, at block 1034, then the weld bead profile is analyzed, at block 1044, so to determine the measured volume, the measured height of the weld bead, the measured rising and falling edges 402, 408 height and/or slope, and/or the like, as discussed in greater detail above. The measurement data is compared to the plurality of predefined parameters, at block 1046, so to determine whether the measured volume, the measured height of the weld bead, the measured rising and falling edges 402, 408 height and/or slope, and/or the like pass. If the measurements do not pass, at block 1046, then the weld bead 302 is designated as defective, at block 1036, the line scan profile 400 measurement data is exported, at block 1038, a reject parts data program may be initiated by the PLC, at block 1040, such that the robot may execute the program to physically remove the defective welded part from the plurality of nests and physically discard the parts into a reject parts area, at block 1018. After the reject parts program at block 1018 is complete, the scan complete is initialized, at block 1010.

On the other hand, if the measurements pass, at block 1046, then the system designates the weld bead as satisfactory, at block 1048, and the line scan profile 400 measurement data is exported, at block 1050.

Then the system determines, at block 1052, whether there are other line scan profiles 400 to analyze. If there are other profiles to analyze, the system begins, at block 1034, to compare the line scan profile 400 with the preliminary predefined parameters. If it is determined, at block 1052, that there are no other line scan profiles 400, then a good parts data program may be initiated by the PLC, at block 1052, such that the robot may execute the program, physically removing the parts from the plurality of nests and placing the parts into a good or satisfactory parts area thus allowing the parts to advance in the manufacturing process, at block 1054. The good parts data program may be any predetermined program using automation to remove parts deemed good or satisfactory by the system. After the good parts program, at block 1056 is complete, the scan complete is initialized, at block 1010.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A system for determining a weld quality comprising:
    a robot having an imaging device configured to generate one or more signals indicative of a weld bead positioned on at least one part;
    a computing device communicatively coupled to the imaging device, the computing device comprising a processor and a non-transitory computer readable memory; and
    a machine-readable instruction set stored in the non-transitory computer-readable memory that causes the computing device to perform at least the following when executed by the processor:
        capture an initial scan to determine a plurality of offset information based on predetermined part features,
        activate the imaging device to capture a scan of the weld bead,
        establish a line scan profile of the weld bead,
        determine that the scan of the weld bead matches a predetermined weld model, and
        analyze the line scan profile to determine a volume of the weld bead, a rising edge of the weld bead, and a falling edge of the weld bead,
        wherein the volume, the rising edge and the falling edge of the weld bead are used to determine that the weld bead has a satisfactory weld quality by comparing the volume, the rising edge and the falling edge of the weld bead to a plurality of predetermined parameters for the weld bead, and wherein when the comparison of the weld bead to the plurality of predetermined parameters is indicative of the satisfactory weld quality, the at least one part is permitted to be advanced by the robot.

2. The system of claim 1, wherein the imaging device is a line scanner configured to scan the weld bead and output the one or more signals corresponding to the line scan profile of the weld bead in three dimensions.

3. The system of claim 1, wherein the volume of the weld bead is a cross-sectional volume.

4. The system of claim 3, wherein the volume of the weld bead is determined by a vertical height of the weld bead between the rising edge and the falling edge in a system vertical direction.

5. The system of claim 4, wherein:
the vertical height of the weld bead is determined from a slope of the rising edge and a slope of the falling edge,
the slope of the rising edge is determined by a first pair of measuring points, one of the first pair of measuring points is positioned at a start of the rising edge and the other one of the first pair of measuring points is positioned at an end of the rising edge, and
the slope of the falling edge is determined by a second pair of measuring points, one of the second pair of measuring points is positioned at a start of the falling edge and the other one of the second pair of measuring points is positioned at an end of the falling edge.

6. The system of claim 1, wherein the machine-readable instruction set further causes the computing device to perform the following when executed by the processor:
determine a pair of boundary lines of the weld bead,
wherein the rising edge of the weld bead and the falling edge of the weld bead are positioned between the pair of boundary lines.

7. The system of claim 6, wherein the machine-readable instruction set further causes the computing device to perform the following when executed by the processor:
analyze the line scan profile for at least one raised surface in a system vertical direction outside of the pair of boundary lines of the weld bead, and
compare the at least one raised surface to a plurality of predetermined parameters for the at least one raised surface to determine a type of the at least one raised surface.

8. The system of claim 7, wherein the at least one raised surface is a weld spike, the weld spike is compared to a predetermined parameter to determine if the weld spike is indicative of the satisfactory weld quality in which the at least one part is permitted to be advanced by the robot.

9. The system of claim 7, wherein:
the at least one raised surface is a first surface of the at least one part sharing the weld bead with a second part to form a combined part in which the first surface of the at least one part is raised above the at least one part or the second part in the system vertical direction,
a height of the at least one raised surface is determined and compared to a predetermined threshold amount, and
the comparison of the at least one raised surface to the predetermined threshold amount is indicative of a placement of the at least one part with reference to the second part, and wherein a satisfactory comparison of the height of the combined part permits the combined part to be advanced by the robot.

10. The system of claim 1, wherein the machine-readable instruction set further causes the computing device to perform the following when executed by the processor:
export the one or more signals indicative of the weld bead to a second computing device communicatively coupled to the robot.

11. A method of determining a weld quality between at least two parts sharing a weld bead comprising:
capturing an initial scan of the at least two parts to determine a plurality of offset information based on predetermined part features;
positioning a robot having an imaging device to scan the weld bead based on the plurality of offset information;
activating the imaging device to capture a scan of the weld bead;
establishing a line scan profile of the weld bead;
determining that the scan of the weld bead matches a predetermined weld model; and
analyzing the line scan profile to determine a volume of the weld bead, a rising edge of the weld bead, and a falling edge of the weld bead.

12. The method of claim 11, wherein:
the volume, the rising edge and the falling edge of the weld bead are used to determine that the weld bead has a satisfactory weld quality by comparing the volume, the rising edge and the falling edge of the weld bead to a plurality of predetermined parameters for the weld bead, and
when the comparison of the weld bead to the plurality of predetermined parameters is indicative of the satisfactory weld quality, the at least two parts sharing the weld bead is permitted to be advanced by the robot.

13. The method of claim 11, wherein the imaging device is a line scanner configured to scan the weld bead and output one or more signals corresponding to the line scan profile of the weld bead in three dimensions.

14. The method of claim 11, wherein the volume of the weld bead is a cross-sectional volume determined by a vertical height of the weld bead between the rising edge and the falling edge in a system vertical direction.

15. The method of claim 14, wherein:
the height of the weld bead is determined from a slope of the rising edge and a slope of the falling edge,
the slope of the rising edge is determined by a first pair of measuring points, one of the first pair of measuring points is positioned at a start of the rising edge and the other one of the first pair of measuring points is positioned at an end of the rising edge, and
the slope of the falling edge is determined by a second pair of measuring points, one of the second pair of measuring points is positioned at a start of the falling edge and the other one of the second pair of measuring points is positioned at an end of the falling edge.

16. The method of claim 11 further comprising determining a pair of boundary lines of the weld bead, and wherein the rising edge of the weld bead and the falling edge of the weld bead are positioned between the pair of boundary lines.

17. The method of claim 16, further comprising:
analyzing the line scan profile for at least one raised surface in a system vertical direction outside of the pair of boundary lines of the weld bead, and comparing the at least one raised surface to a plurality of predetermined parameters for the at least one raised surface to determine a type of the at least one raised surface.

18. The method of claim 17, wherein the at least one raised surface is a weld spike, the weld spike is compared to a predetermined parameter to determine if the weld spike is indicative of the satisfactory weld quality in which the at least two parts is permitted to be advanced by the robot.

19. The method of claim 17, wherein:

the at least one raised surface is a first surface of one of the at least two parts sharing the weld bead to form a combined part in which the first surface the one of the at least two parts is raised above the other one of the at least two parts in the system vertical direction, a height of the at least one raised surface is determined and compared to a predetermined threshold amount, the comparison of the at least one raised surface to the predetermined threshold amount is indicative of a placement of the at least two parts together sharing the weld bead forming the combined part, and a satisfactory comparison of the height of the combined part permits the combined part to be advanced by the robot.

20. A system for determining a weld quality comprising:

a robot having an imaging device configured to generate one or more signals indicative of a quality of a weld bead joining at least two parts into a combined part;

a computing device communicatively coupled to the imaging device, the computing device comprising a processor and a non-transitory computer readable memory; and a machine-readable instruction set stored in the non-transitory computer-readable memory that causes the computing device to perform at least the following when executed by the processor:

capture an initial scan of the at least two parts to determine a plurality of offset information based on predetermined part features, position the robot having an imaging device to scan the weld bead based on the plurality of offset information, activate the imaging device to capture a scan of the weld bead, establish a line scan profile of the weld bead, determine that the scan of the weld bead matches a predetermined weld model, analyze the line scan profile to determine a volume of the weld bead, a rising edge of the weld bead, and a falling edge of the weld bead, and compare the volume of the weld bead, the rising edge of the weld bead, and the falling edge of the weld bead to predetermined parameters such that a positive comparison of the weld bead to the plurality of predetermined parameters is indicative of the satisfactory weld quality, wherein in response, the combined part is permitted to be advanced by the robot.

* * * * *